(12) United States Patent
Crutchfield et al.

(10) Patent No.: US 9,061,163 B2
(45) Date of Patent: Jun. 23, 2015

(54) FAULT TOLERANT SYSTEM FOR AN IMPLANTABLE CARDIOVERTER DEFIBRILLATOR OR PULSE GENERATOR

(75) Inventors: Randolph E. Crutchfield, Scottsdale, AZ (US); Lonny V. Cabelka, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

(21) Appl. No.: 13/014,958

(22) Filed: Jan. 27, 2011

(65) Prior Publication Data

US 2012/0197330 A1    Aug. 2, 2012

(51) Int. Cl.
| | | |
|---|---|---|
| A61N 1/362 | (2006.01) | |
| A61N 1/368 | (2006.01) | |
| A61N 1/36 | (2006.01) | |
| A61N 1/39 | (2006.01) | |
| A61N 1/378 | (2006.01) | |

(52) U.S. Cl.
CPC ............ *A61N 1/3931* (2013.01); *A61N 1/3684* (2013.01); *A61N 1/3686* (2013.01); *A61N 1/3782* (2013.01); *A61N 1/3962* (2013.01); *A61N 1/3981* (2013.01)

(58) Field of Classification Search
USPC ................................................ 607/5, 34, 48
See application file for complete search history.

(56) References Cited

U.S. PATENT DOCUMENTS

| | | | |
|---|---|---|---|
| 4,628,934 A | 12/1986 | Pohndorf et al. | |
| 5,003,975 A | 4/1991 | Hafelfinger et al. | |
| 5,014,705 A | 5/1991 | Graupe et al. | |
| 5,061,911 A | 10/1991 | Weidman et al. | |
| 5,281,219 A | 1/1994 | Kallok | |
| 5,318,593 A | 6/1994 | Duggan | |
| 5,387,228 A | 2/1995 | Shelton | |
| 5,591,211 A * | 1/1997 | Meltzer .............................. 607/5 |
| 5,800,465 A | 9/1998 | Thompson et al. | |
| 5,895,416 A | 4/1999 | Barreras, Sr. et al. | |
| 6,070,101 A | 5/2000 | Struble et al. | |
| 6,082,367 A | 7/2000 | Greeninger et al. | |
| 6,225,797 B1 | 5/2001 | Willis et al. | |
| 6,687,542 B2 | 2/2004 | Kroll | |
| 7,142,919 B2 | 11/2006 | Hine et al. | |
| 7,184,833 B2 | 2/2007 | Ganion et al. | |
| 7,532,936 B2 | 5/2009 | Erickson et al. | |
| 7,713,194 B2 | 5/2010 | Zdeblick | |
| 7,768,151 B2 | 8/2010 | Andreu et al. | |
| 2003/0204226 A1 * | 10/2003 | Acosta et al. ................... 607/48 |
| 2005/0075677 A1 * | 4/2005 | Ganion et al. .................... 607/9 |
| 2007/0265671 A1 | 11/2007 | Roberts et al. | |

FOREIGN PATENT DOCUMENTS

GB    2349091 A    10/2000

OTHER PUBLICATIONS

P0036982.WOU1 (PCT/US2012/021151) PCT Notification of Transmittal of the International Search Report and the Written Opinion of the International Searching Authority, Mailed May 10, 2012, 14 pages.

* cited by examiner

*Primary Examiner* — Carl H Layno
*Assistant Examiner* — Jon Eric C Morales
(74) *Attorney, Agent, or Firm* — Evans M. Mburu (57) ABSTRACT

The disclosure describes circuits for providing therapy in an implantable medical device. The illustrative circuits include features that provide fault tolerance with graceful degradation as well as switching control methods that reduce component count and improves reliability.

32 Claims, 8 Drawing Sheets

| Pacing Vector | LV FET Gates | | | Ring Switch |
|---|---|---|---|---|
| | LVR1 | LVR2 | LVR3 | |
| LVT-LVR1* | V+ | gnd | gnd | on |
| LVT-LVR2 | gnd | V+ | gnd | on |
| LVT-LVR3 | gnd | gnd | V+ | on |

FIG. 8

| Pacing Vector | LV FET Gates | | | | Ring Switches | |
|---|---|---|---|---|---|---|
| | LVT | LVR1 | LVR2 | LVR3 | Bank A | Bank B |
| LVT-LVR1* | V+ | V+ | V- | V- | off | on |
| LVT-LVR3 | V+ | V- | V- | V+ | off | on |
| LVR1-LVT | V+ | V+ | V- | V- | on | off |
| LVR1-LVR2 | V- | V+ | V+ | V- | on | off |
| LVR2-LVR1 | V- | V+ | V+ | V- | off | on |
| LVR2-LVR3 | V- | V- | V+ | V+ | off | on |
| LVR3-LVT | V+ | V- | V- | V+ | on | off |
| LVR3-LVR2 | V- | V- | V+ | V+ | on | off |

FIG. 9

FAULT TOLERANT SYSTEM FOR AN IMPLANTABLE CARDIOVERTER DEFIBRILLATOR OR PULSE GENERATOR

FIELD

The present disclosure relates to implantable medical devices. More specifically, the disclosure relates to implantable medical device systems and circuitry that include fault tolerance with graceful degradation.

BACKGROUND

There are a number of implantable medical devices (IMDs) that sense various physiological parameters and/or provide a variety of therapies. For example, implantable pulse generators (IPG) typically include one or more medical electrical leads that are in contact with cardiac tissue to sense electrical depolarization and provide pacing therapy stimuli. Implantable cardioverter/defibrillators (ICD) also typically include one or more medical electrical leads and provide a larger therapy stimulus for cardioversion or to defibrillate the heart. Often, IMDs include both pacing therapy and cardioversion/defibrillation therapy capabilities.

A housing containing the pulse generator, battery, capacitors, processor, memory, circuitry, etc. is implanted subcutaneously. One or more of the leads are delivered transvenously such that electrodes forming a portion of the lead are disposed within or contacting an outer portion of the heart. The housing, or "can", may also include one or more electrodes that are selectively used in combination with the various lead electrodes.

In general, the leads sense electrical activity of the heart, typically represented as an electrogram (EGM), which is indicative of the cardiac depolarization waveform and indicates the timing of the various components of the cardiac cycle. This data indicates whether and when intrinsic events occur, their duration and morphology. The timing of certain events (or their failure to occur when expected) is used to trigger various device actions. For example, sensing an atrial depolarization may begin a timer (an escape interval) that leads to a ventricular pacing pulse therapy upon expiration. In this manner, the ventricular pacing therapy is coordinated with respect to the atrial event.

The heart includes four chambers; specifically a right and a left atrium and a right and left ventricle. Leads are commonly and routinely placed into the right atrium as well as the right ventricle. For left sided applications, the lead is typical guided through the coronary sinus and into a cardiac vein. One or more electrodes are then positioned (within the vein) to contact an outer wall of the left atrium and/or left ventricle. Other methods include direct access to the interior of the left atrium and left ventricle through the septal wall.

The therapy delivery circuit in a typical IMD uses at least two capacitors to deliver the therapy stimulus. The sequence is started by charging a capacitor (known as the hold capacitor) to the desired therapy stimulus voltage. Another capacitor (known as the tip capacitor) is typically connected to the tip electrode of the medical lead implanted in the heart. The medical lead has another electrode known as a ring electrode allowing current from the tip electrode to pass through the heart and return to the IMD. During the first phase of a pace therapy stimulus, the previously charged hold capacitor is connected in series with the tip capacitor and the ring electrode. The uncharged tip capacitor begins charging from the hold capacitor. This current passes through the heart (tip-ring electrodes) and provides the therapy stimulus. The second phase connects the tip capacitor to ground allowing the capacitor to discharge. Again, this current passes through the heart and creates the opposite polarity second phase.

In a typical device, this delivery circuit is replicated for each of the leads as necessary with each hold and tip capacitor pair being dedicated to a particular electrode. A need therefore exists for a reduction in the number of components employed by the IMD.

SUMMARY

By no longer having dedicated components, the total component count can be reduced. An additional benefit of aspects of the present disclosure of obviating the need for dedicated components, is that the system is able to tolerate failure of one or more components.

In accordance with an embodiment of the present disclosure, a plurality of non-dedicated hold capacitors and tip capacitors are provided. One or more switch arrays are coupled to the plurality of non-dedicated hold capacitors and tip capacitors to select one or more of the plurality of non-dedicated hold capacitors and tip capacitors and connect them to an electrode of a medical electrical lead.

In some embodiments, fault detection circuitry is provided to monitor the plurality of non-dedicated hold capacitors and tip capacitors and generate a signal that controls the selection of the one or more hold capacitors and tip capacitors. In some embodiments, a notification is generated upon detection of an abnormality of a capacitor. In yet other embodiments, an algorithm or state machine is employed to provide graceful degradation of functionality upon detection of an abnormality.

DETAILED DESCRIPTION

Figure 1:
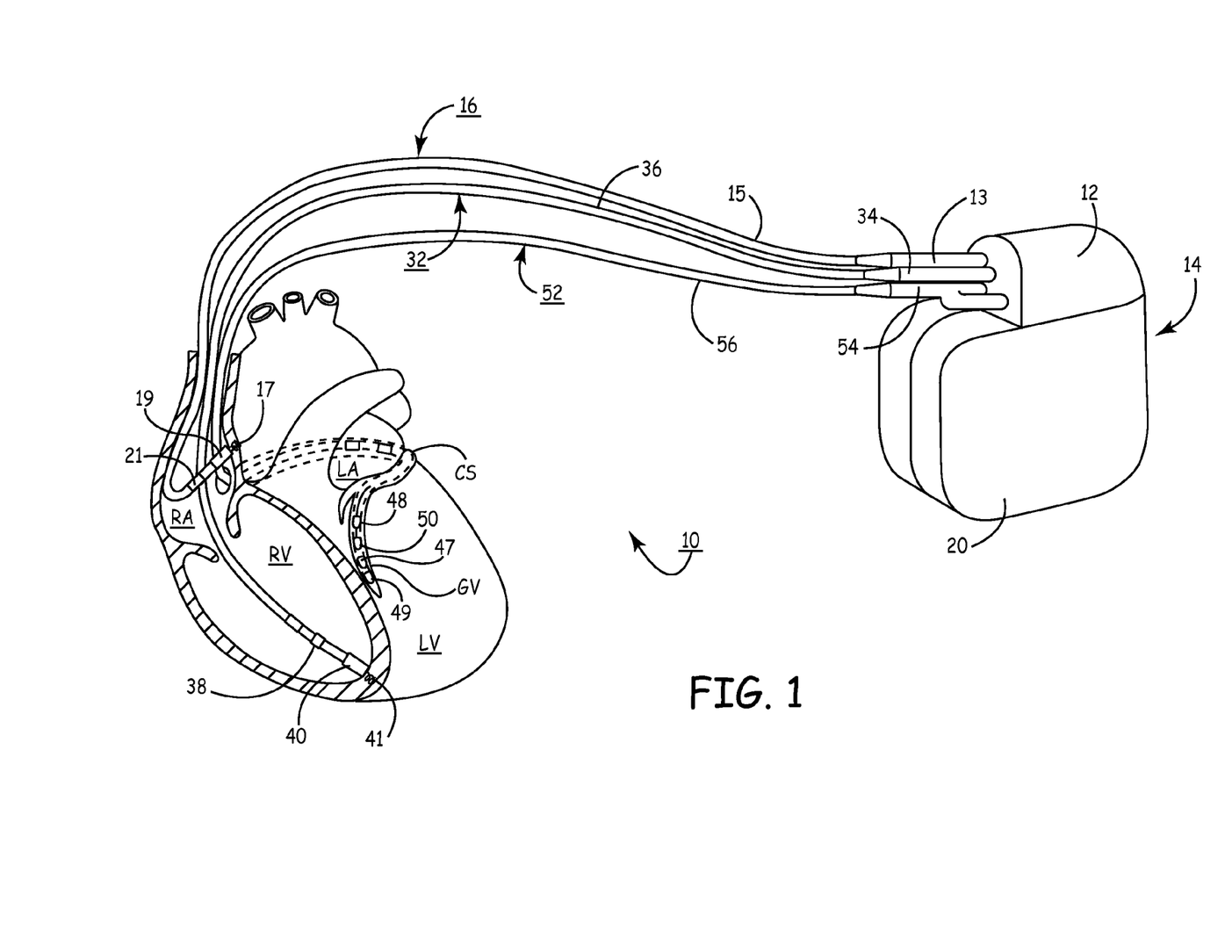
FIG. 1 is a schematic diagram depicting a three-channel, atrial and bi-ventricular, pacing system for implementing the present disclosure.

In the following detailed description, references are made to illustrative embodiments of implantable medical devices and therapy delivery circuitry for delivery of pacing and cadioversion/defibrillation therapy (collectively referred to herein as stimulus therapy) with the devices. The detailed description is to be read with reference to the figures, in which like elements in different figures have like reference numerals. The figures, which are not necessarily to scale, depict embodiments and are not intended to limit the scope of the disclosure. For the purposes of clarity, the same reference numbers are used in the drawings to identify similar elements FIG. 1 is a schematic representation of a system 10 comprising a triple-chamber implantable medical device (IMD) 14 and associated implantable medical electrical leads 16, 32, 52 in which the present disclosure may be practiced. The IMD 14 is implanted subcutaneously in a patient's body between the skin and the ribs. The three leads 16, 32, 52 operatively couple the IMD 14 with the right atrium (RA), the right ventricle (RV) and the left ventricle (LV), respectively. Each lead has at least one electrical conductor and electrode, and a remote indifferent can electrode 20 is formed as part of the outer surface of the housing of the IMD 14. The lead electrodes and the remote indifferent can electrode 20 can be selectively employed to provide a number of unipolar and bipolar electrode combinations for pacing and sensing functions, particularly sensing far field signals (e.g. far field R-waves). The depicted positions in or about the right and left heart chambers are also merely exemplary. Moreover other leads and electrodes may be used instead of those depicted in FIG. 1 that are adapted to be placed at electrode sites on or in or relative to the RA, LA, RV and LV. In addition, mechanical and/or metabolic sensors can be deployed independent of, or in tandem with, one or more of the depicted leads.

As depicted, a bipolar RA lead 16 passes through a vein into the RA chamber of the heart 10, and the distal end of the RA lead 16 is attached to the RA wall by an attachment mechanism 17. The bipolar RA lead 16 is formed with an in-line connector 13 fitting into a bore of IMD connector block 12 that is coupled to a pair of electrically insulated conductors within lead body 15 and connected with distal tip RA electrode 19 and proximal ring RA electrode 21. Delivery of atrial pace pulses and sensing of atrial sense events is effected between the distal tip RA electrode 19 and proximal ring RA electrode 21, wherein the proximal ring RA electrode 21 functions as an indifferent electrode. Alternatively, a unipolar RA lead could be substituted for the depicted bipolar RA lead 16 and be employed with the indifferent can electrode 20. Or, one of the distal tip RA electrode 19 and proximal ring RA electrode 21 can be employed with the indifferent can electrode 20 for unipolar pacing and/or sensing.

Bipolar RV lead 32 is passed through the vein and the RA chamber of the heart 10 and into the RV where its distal ring and tip RV electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV electrode 40 and proximal ring RV electrode 38, wherein the proximal ring RV electrode 38 functions as an indifferent electrode. Alternatively, a unipolar RV lead could be substituted for the depicted bipolar RV lead 32 and be employed with the indifferent can electrode 20. Or, one of the distal tip RV electrode 40 and proximal ring RV electrode 38 can be employed with the indifferent can electrode 20 for unipolar pacing and/or sensing.

The quadrapolar, endocardial coronary sinus (CS) lead 52 is passed through a vein and the RA chamber of the heart 10, into the coronary sinus and then inferiorly in a branching vessel of the great cardiac vein to extend the proximal and distal LV CS electrodes 47, 48, 49 and 50 alongside the LV chamber. The distal end of such a CS lead is advanced through the superior vena cava, the right atrium, the ostium of the coronary sinus, the coronary sinus, and into a coronary vein descending from the coronary sinus, such as the lateral or posteriolateral vein. In addition, while not depicted in FIG. 1 the atrial, ventricular, and/or CS-deployed pacing leads can couple to the exterior of a heart via a pericardial or epicardial attachment mechanism.

In the embodiment, LV CS lead 52 bears proximal LV CS electrodes 48 and 50 and distal LV CS electrodes 47 and 49, all positioned along the left ventricle. The LV CS leads may not employ any fixation mechanism and instead rely on the close confinement within the vessel to maintain the electrode or electrodes at a desired site. The LV CS lead 52 is formed with a multiple conductor lead body 56 coupled at the proximal end connector 54 fitting into a bore of IMD connector block 12. A portion of the lead body 56 may be selected to have a small diameter in order to lodge the LV CS electrodes deeply in a vein branching from the great vein (GV). In this case, the CS lead body 56 would encase four electrically insulated lead conductors extending proximally from the more proximal LV CS electrode(s) and terminating in a dual bipolar connector 54. The quadrapolar lead 52 may provide the capability to steer the stimulation pulse away from the phrenic nerve while still providing LV stimulation.

It will be understood that LV CS lead 52 could also be a conventional, unipolar or bipolar, type lead bearing a single LV CS electrode 48 and/or a dual LV CS electrodes 48 and 50 that are paired with the indifferent can electrode 20 or the ring electrodes 21 and 38, respectively for pacing and sensing in the LA and/or LV, respectively. With such a configuration pacing stimuli is selectively delivered to the right atrium, the right ventricle, and/or the left ventricle. Also, although leads 16, 32, 52 have been illustrated as pacing leads, additional electrodes could be placed on these leads to generate a defibrillation pulse, such that the defibrillation waveform traverses the desired portion of the heart 10.

Figure 2:
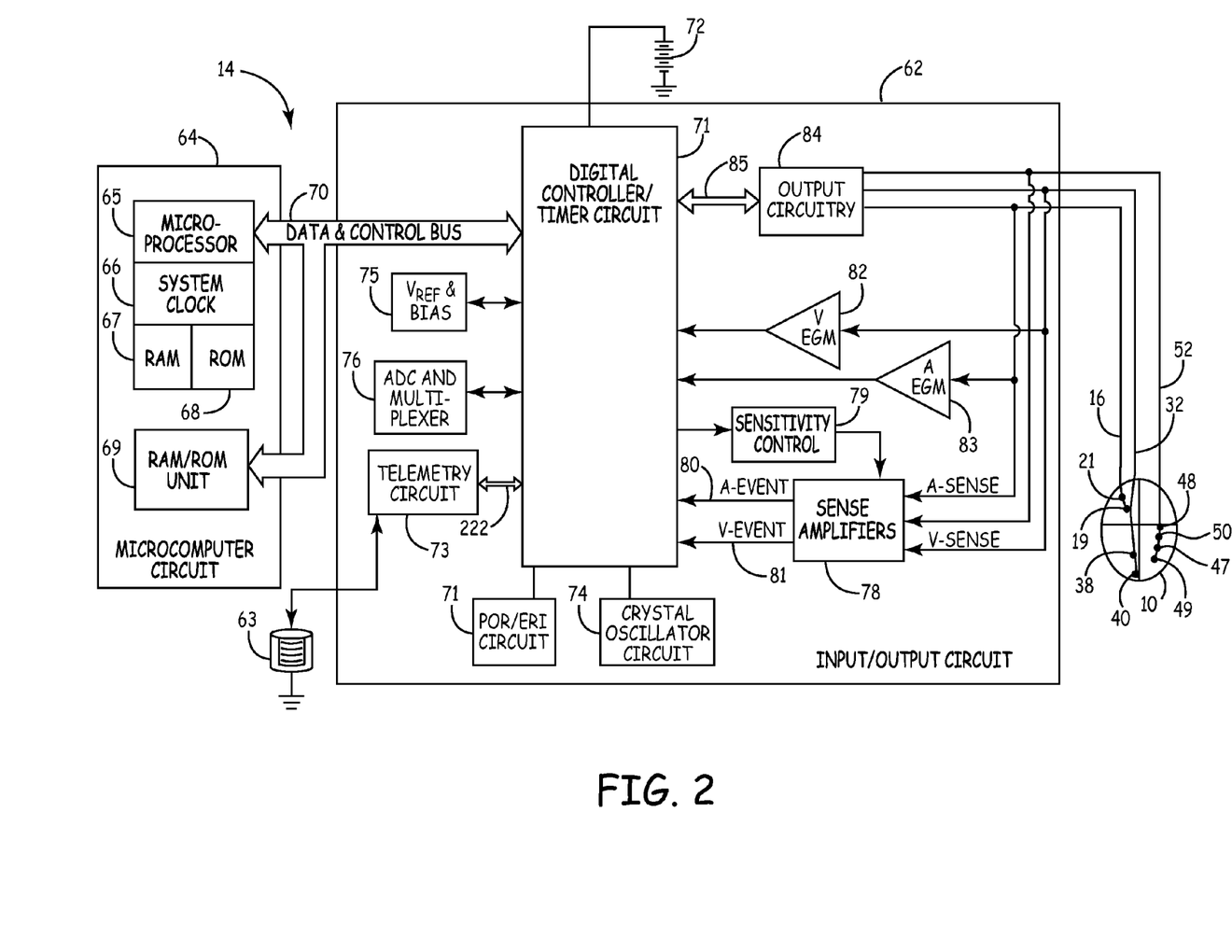
FIG. 2 is a simplified block diagram of one embodiment of IMD circuitry and associated leads employed in the system of FIG. 1 for providing three sensing channels and corresponding pacing channels that selectively functions in a ventricular pacing mode providing ventricular capture verification according to the present disclosure.

FIG. 2 is a simplified schematic diagram illustrating certain components of the IMD 14 of FIG. 1. Although a particular implementation is disclosed herein, it is to be understood that the present disclosure may be advantageously practiced in conjunction with many different types of implantable devices, such as implantable neurological stimulators.

IMD 14 is schematically shown to be electrically coupled via leads 16, 32, 52 to a patient's heart 10. As discussed in conjunction with FIG. 1, leads 16, 32, 52 include one or more electrodes, depending upon whether they are unipolar or bipolar leads. As would be appreciated by those of ordinary skill in the art, bipolar leads include separate, electrically isolated tip and ring electrodes, while unipolar leads include a single tip electrode. For the sake of illustration, electrode pairs designated as 38, 40; 19, 21; and 47, 48, 49, 50 are shown in FIG. 2, located near their distal ends of leads 16, 32, 52, respectively, and positioned within the right ventricular (RV), right atrial (RA) and left ventricular (LV) chambers, respectively, of heart 10. It is to be understood, however, that leads 16, 32, 52 may be of either the unipolar or bipolar type as is well known in the art. Electrodes 38, 40, 19, 21, 47, 48, 49 and 50 are coupled via suitable lead conductors through input/output terminals of an input/output circuit 62. In alternative embodiments, an activity sensor may be electrically coupled to the IMD, in accordance with common practice in the art. The output from such an activity sensor may be coupled to input/output circuit 62 to provide signals for controlling the rate response of the IMD 14.

Input/output circuit 62 contains the analog circuits for interface to the heart 10, an antenna 63, as well as circuits for the application of stimulating therapy to heart 10 to control its rate as a function thereof under control of the software-implemented algorithms in a microcomputer circuit 64.

Microcomputer circuit 64 comprises a microprocessor 65 having an internal system clock circuit 66, and on-board RAM 67 and ROM 68. Microcomputer circuit 64 further comprises a RAM/ROM unit 69. Microprocessor 65 and RAM/ROM unit 69 are each coupled by a data and control bus 70 to a digital controller/timer circuit 71 within input/output circuit 62. Microcomputer circuit 64 may be a commercially-available, general-purpose microprocessor or microcontroller, or may be a custom integrated circuit device augmented by standard RAM/ROM components. Microcomputer circuit 64 controls the timing sensing and therapy delivery functions and other device functions in accordance with a programmed operating mode.

It will be understood that each of the electrical components represented in FIG. 2 is powered by an appropriate implantable battery power source 72, in accordance with common practice in the art. In the presently disclosed embodiment of the disclosure, power source 72 is a lithium-iodine battery. Lithium-iodine batteries suitable for the purposes of the present disclosure are well-known and commercially-available from a number of manufacturers. For the sake of clarity, the coupling of battery power to the various components of IMD 14 has not been shown in the Figures.

IMD 10 is programmable by means of an external programming unit (not shown). To facilitate communication with the external programming unit and other external devices, an antenna 63 is connected to input/output circuit 62 for purposes of telemetry through an RF telemetry circuit 73 in accordance with one embodiment of the disclosure. In the embodiment, telemetry circuit 73 is coupled to digital controller/timer circuit 71. It is contemplated that telemetry circuit 73 may also be coupled directly to microcomputer circuit 64 via data and control bus 70.

A crystal oscillator circuit 74 provides main timing clock signals to digital controller/timer circuit 71. A $V_{REF}$ and Bias circuit 75 generates stable voltage reference and bias currents for the analog circuits of input/output circuit 62. An analog-to-digital converter (ADC) and multiplexer unit 76 digitizes analog signals and voltages to provide "real-time" telemetry intracardiac signals and battery elective replacement indicator (ERI) and end-of-life (EOL) functions.

A power-on-reset and elective replacement indicator (POR/ERI) circuit 77 functions as a means to reset circuitry and related functions to a default condition upon detection of a low battery condition, which will occur upon initial device power-up or will transiently occur in the presence of electromagnetic interference, for example. POR/ERI circuit 77 also functions to monitor the depth of discharge of battery 72 and informs digital controller/timer circuit 71 when an ERI should be issued.

The operating commands for controlling the timing of IMD 14 are coupled by bus 70 to digital controller/timer circuit 71 wherein digital timers, registers, and counters are employed to establish the overall escape interval of the pacemaker, as well as various refractory, blanking, and other timing windows for controlling the operation of the peripheral components within input/output circuit 62.

Digital controller/timer circuit 71 may also be coupled to sensing circuitry including a sense amplifier circuit 78 and a sensitivity control circuit 79. In particular, digital controller/timer circuit 71 receives an A-EVENT (atrial event) signal on line 80, and a V-EVENT (ventricular event) signal on line 81. Sense amplifier circuit 78 is coupled to leads 16, 32, 52, in order to receive the V-SENSE (ventricular sense) and A-SENSE (atrial sense) signals from heart 10.

Sense amplifier circuit 78 asserts the A-EVENT signal on line 80 when an atrial event (i.e., a paced or intrinsic atrial event) is detected, and asserts the V-EVENT signal on line 81 when a ventricular event (paced or intrinsic) is detected. Sense amplifier circuit 78 includes one or more sense amplifiers. Sensitivity control 79 is provided to adjust the gain of sense amplifier circuitry 78 in accordance with programmed sensitivity settings, as would be appreciated by those of ordinary skill in the pacing art.

A V-EGM (ventricular electrocardiogram) amplifier 82 is coupled to a conductor in lead 32 to receive a V-SENSE signal from heart 10. Similarly, an A-EGM (atrial electrocardiogram) amplifier 83 is coupled to one conductor of lead 16 to receive the A-SENSE signal from heart 10. A representation of the analog electrogram signals of the patient's electrical heart activity developed by V-EGM amplifier 82 and A-EGM amplifier 83 may be stored for subsequent retrieval and transmission by uplink telemetry via an external programmer (not shown) and/or directly transmitted on those occasions when the implanted device is being interrogated by the external programmer.

Digital controller and timer circuit 71 is coupled to an output circuit 84 (described in more detail below) via a plurality of control lines designated collectively as 85. Controller circuit 71 provides signals to various components of output circuit 84 for delivery of therapy to heart 10. In particular, and as will be described below in greater detail, various capacitors (not shown in FIG. 2) for storage of energy for therapy delivery may be supplied with the energy by battery 72 and discharged across heart 10. Output circuit 84 is also coupled to one or more of the conductors in each lead 16, 32, 52. For delivering electrical stimulation pulses, output circuit 84 may be coupled to electrodes on one or more of the leads 16, 32, 52 through the conductors. Output circuit 84 selects which electrodes and corresponding polarities are used for delivering electrical stimulation pulses.

Digital controller/timer circuit 71 provides signals on lines 85 to output circuit 84 indicating whether unipolar or bipolar pacing has been selected for the atrial and ventricular chambers. Output circuit 84 responds to these signals by coupling the appropriate lead conductors to establish the desired current path for therapy delivery. For example, if bipolar atrial pacing is selected, output circuit 84 will function to couple the two conductors of bipolar atrial lead 16, so that atrial pacing pulses are delivered between the two atrial electrodes. If unipolar atrial pacing is selected, output circuit 84 functions to couple the unipolar pacing electrode on lead 16 and the pacemaker's conductive outer canister 20, so that atrial pacing pulses are delivered between the atrial tip electrode and the canister, acting as a common electrode.

As would be appreciated by those of ordinary skill in the art, input/output circuitry will include decoupling circuitry for temporarily decoupling sense amplifier circuit 78, V-EGM amplifier 82 and A-EGM amplifier 83 from leads 16, 32, 52 when stimulating pulses are being delivered from output circuit 84. For the sake of clarity, such decoupling circuitry is not depicted in FIG. 2.

Digital controller/timer circuit 71 includes certain registers for storing digital data used in the control of IMD 14 functions. For example, one of the registers maintained in digital controller/timer circuit 71 in accordance with the presently disclosed embodiment of this disclosure is an eight-bit atrial output control register. Digital controller/timer circuit 71 uses the data in the atrial output control register to control various aspects of atrial pacing by IMD 14. In the case of programmable functions, the digital data representing selected values for programmable parameters are downloaded from an external programming device to IMD 14 via the telemetry link. As would be appreciated by those of ordinary skill in the art, a downloaded digital value can contain bits identifying the parameter to be programmed and bits identifying the selected value for that parameter.

While specific embodiments of the components and circuitry in IMD 14 have been identified herein, this is done for the purposes of illustration only. It is believed that the specific embodiments of such circuits are not critical to the implementation of the present disclosure, nor are they critical to an understanding of the present disclosure. For example, implementations useful for cardiac purposes need only provide means for generating a therapy and/or detecting signals indicative of natural and/or stimulated contractions of the heart. It is also believed that those of ordinary skill in the art could chose from among the various well-known implementations of such circuits in practicing the present disclosure.

As will be appreciated by those of ordinary skill in the art, the application of a therapy to one chamber of the heart is a multiple-step process. The process is initiated by digital controller/timer circuit 71 in response to a predetermined set of conditions. For example, controller/timer circuit 71 may function to initiate delivery of a ventricular pacing pulse only when a predetermined time interval elapses following a paced or natural atrial event, when no natural ventricular event is detected during that time period. It is believed that the details of the pacing algorithm, i.e., the various conditions, time intervals, algorithms, and the like that define the pacing functions of IMD 14, are not critical to an understanding of the present disclosure, and will not be described herein in substantial detail. It is believed that various pacing algorithms and implementations of pacemakers are known and/or commercially available, and that the present disclosure may be readily adapted for use in different systems by persons having the benefit of the present disclosure. For the purposes of the present disclosure, it is sufficient to state that digital controller/timer circuit 71 implements an algorithm and at various times takes steps to initiate delivery of therapy, alone, or in conjunction with microcomputer circuit 64.

Figure 3:
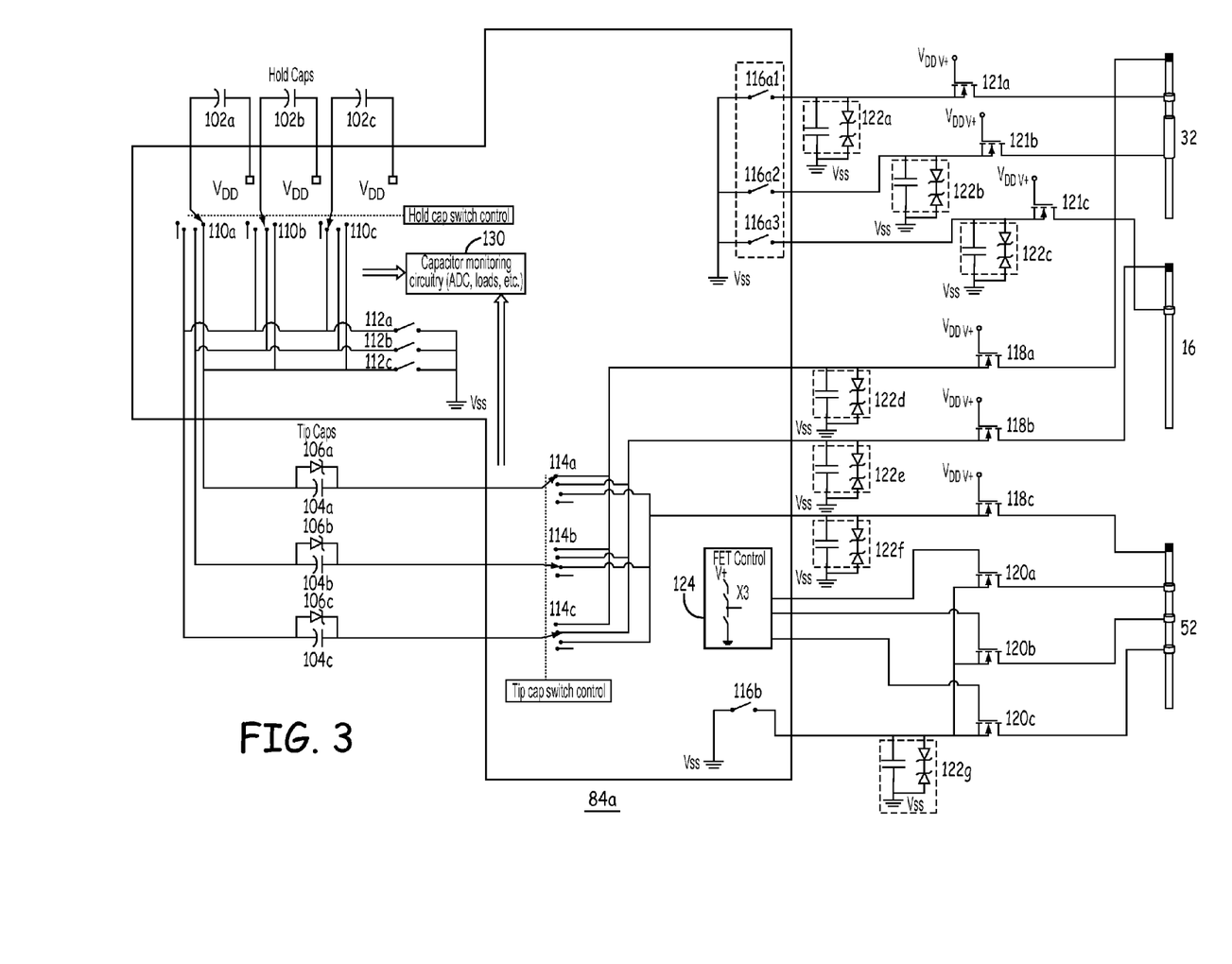
FIGS. 3-5 depict schematic diagrams for output circuits in accordance with illustrative embodiments of the present disclosure.
Figure 4:
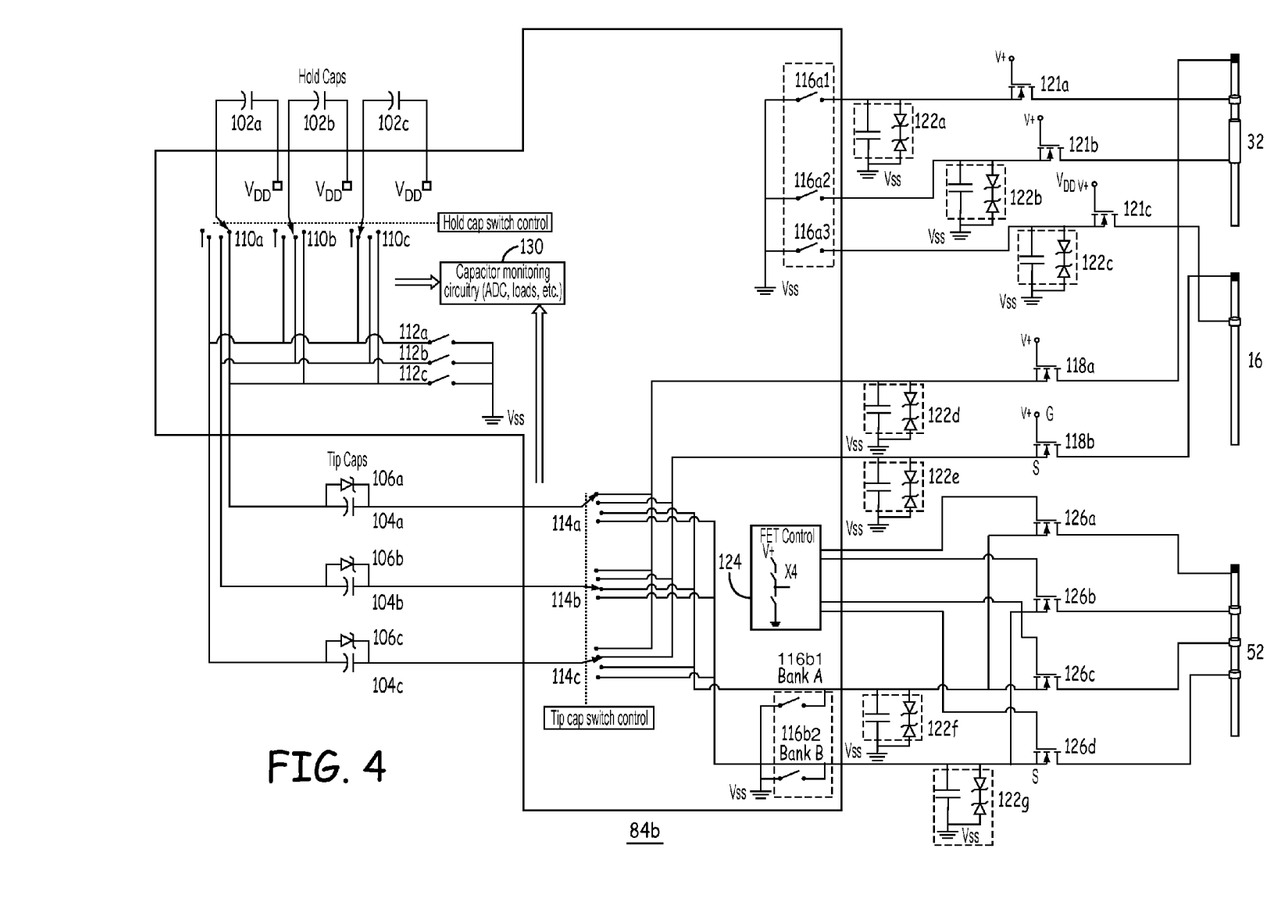
Figure 5:
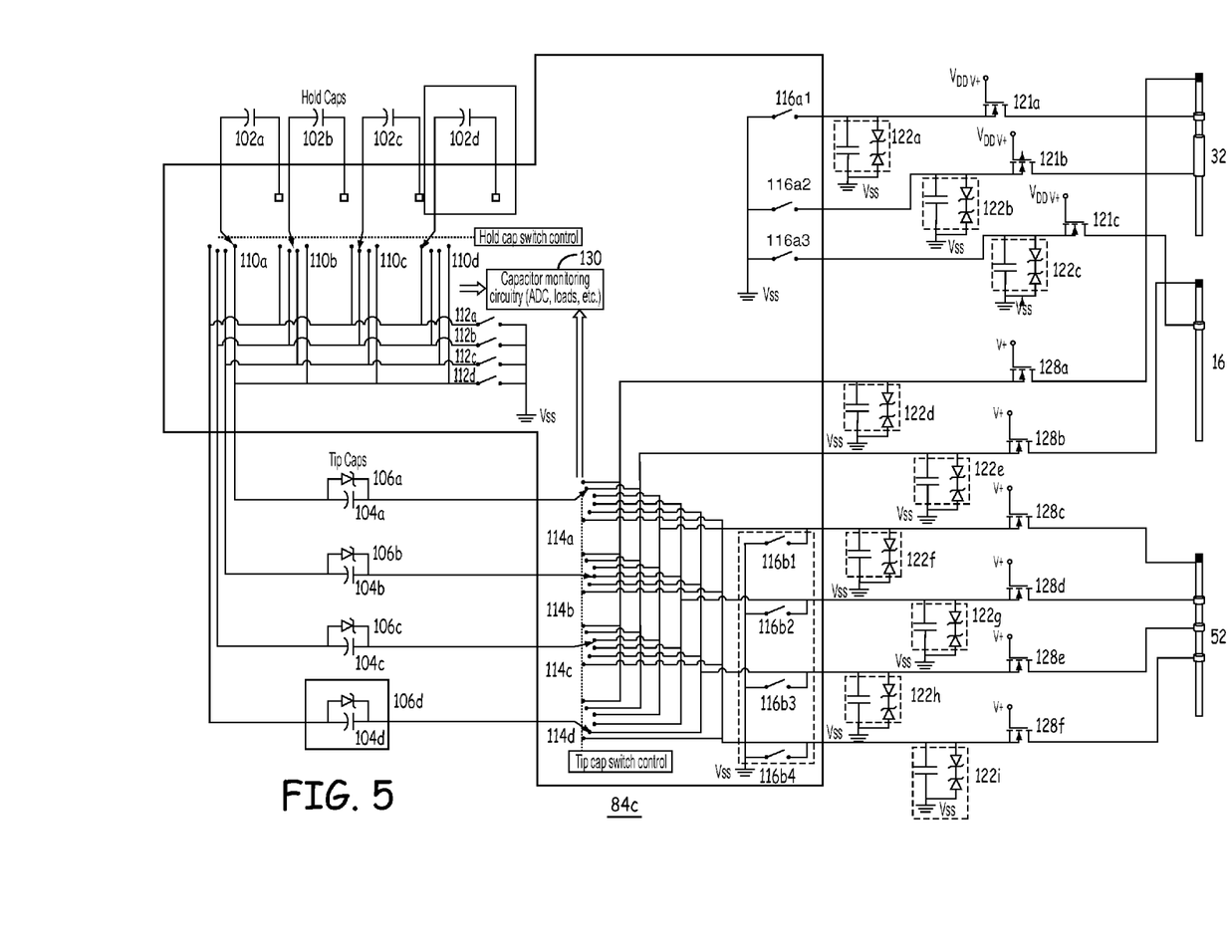

FIGS. 3, 4, and 5 illustrate schematic diagrams for output circuits 84 in accordance with embodiments of the present disclosure. As explained previously, the conventional output circuits utilize a dedicated pair of capacitors for each therapy (pacing or cadioversion/defibrillation stimulus) output channel coupled to an electrode. The illustrative embodiments of FIGS. 3, 4, and 5 utilize non-dedicated capacitors with control circuitry for selection of appropriate capacitor pairs to form a therapy output channel.

With that in mind, the exemplary circuit of FIG. 3 shows an output circuit 84a that includes a plurality of hold capacitors 102a,102b,102c (collectively "hold capacitors 102"). Hold capacitors 102 may be selectively coupled, on the positive side, to the output of a charge pump (not shown) that has been programmed to the desired pacing voltage. A first plurality of switches 110a, 110b, 110c (collectively "first switching array 110") are coupled to the negative terminals on the hold capacitors 102. Specifically, each of the hold capacitors 102a, 102b, 102c is coupled to a respective one of switches 110a, 110b, 110c. The first switching array 110 is selectively closed to couple the hold capacitors 102 in series to a plurality of tip capacitors 104a, 104b, 104c (collectively "tip capacitors 104") to charge the tip capacitors 104 during a first phase of therapy delivery. Each of the tip capacitors 104 may be placed in parallel with zener diodes 106a, 106b, 106c, (collectively "zener diodes 106"), with the zener diodes 106 being selected to control the voltage established on the tip capacitors 104. As such, the zener diodes 106 will limit the reverse bias voltage seen on the capacitors 104.

During the second phase of therapy delivery, tip capacitor 104 is decoupled from switching array 110 and is coupled to a first set of ground switches 112a-c for connection to the negative ($V_{SS}$) or ground terminal. When coupled to the $V_{SS}$ terminal, the discharging of the tip capacitors 104 is initiated.

Turning then to an illustrative therapy delivery sequence in accordance with an embodiment of the present disclosure, the desired combination of hold capacitor 102 and tip capacitor 104 is selected. The therapy delivery sequence is initiated by charging the selected one of hold capacitors 102 to the desired voltage. When controller/timer circuit 71 initiates delivery of a therapy, it asserts one or more signals conducted on lines 85 to initiate the charging of the appropriate hold capacitor 102. The charging of the hold capacitor 102 may be through conventional methods such as that described in U.S. Pat. No. 5,387,228, issued to Shelton, which is incorporated herein by reference in its entirety. Subsequently, the positive terminal of the charged hold capacitor 102 is switched to ground. Digital controller/timer circuit 31 also issues control signals causing the actuation of the appropriate switch on the first switching array 110 to selectively couple one of the tip capacitors 104 to the charged hold capacitor 102.

The selected one of tip capacitors 104 is then connected to an electrode of the medical leads 16, 32, 52 implanted in the heart (as will be discussed further below). Therefore, after the desired voltage has been stored on the selected hold capacitor 102 a first phase is initiated to pump charge to the desired tip capacitor 104. The first phase delivers a therapy having a first polarity (in this case, negative) to the patient. Digital controller/timer circuit 71 also asserts the appropriate signals on lines 85 to cause the tip capacitor 104 to be momentarily coupled to the appropriate conductor(s) of one of the leads 16, 32, 52 for therapy delivery through the corresponding electrode coupled to the conductor. For purposes of understanding the inventive aspects of this disclosure, the choice of electrode to which the given tip capacitor 104 is coupled is believed to be non-consequential. In other words, while it is important to determine whether the tip capacitor 104 is coupled to a tip electrode or a ring electrode it is sufficient to note that several circumstances must be taken into account in determining which of those electrodes should be coupled to the tip capacitor 104 but those circumstances are not essential to understanding the present disclosure and will therefore not be discussed for ease of description.

The tip capacitors 104 are coupled to a second plurality of switches 114a,114b,114c, (collectively "second switching array 114"). The second switching array 114 functions to couple any of the tip capacitors 104 to any one of the electrodes on leads 16, 32, 52 through respective conductors within the leads. In the embodiment, none of the tip capacitors 104 is dedicated to any one of the electrodes on leads 16, 32, 52. Rather, the second switching array 114 is controlled to couple the appropriate tip capacitor(s) 104 with the desired electrode(s) on leads 16, 32, 52 thereby facilitating the interchangeability of each of tip capacitors 104.

With the above in mind, a therapy output channel, in the conventional sense, is defined at least in part by the pair of the selected hold capacitor 102 coupled via the first switching array 110 to the selected tip capacitor 104. While not illustrated for the sake of clarity, those skilled in the art will recognize that the flexibility provided by the switching array 110 facilitates the selection of multiple combinations of hold capacitor 102 to tip capacitor 104 in defining the therapy output channel as well as enabling the creation of multiple therapy output channels.

An added benefit of the concepts presented in this disclosure is that the first switching array 110 and the second switching array 114 may be suitably employed to bypass hold capacitors 102 or tip capacitors 104. In that regard, the need may arise to directly couple the energy source, battery 72, to tip capacitor 104. It should be understood that such a resulting arrangement also forms a therapy output channel. Those skilled in the art can therefore envision additional traces being created in the illustrative circuit to implement a modified therapy output channel.

Turning back to FIG. 3, output circuit 84a includes a first plurality of field effect transistors 118a-c (collectively "FETs 118") that are coupled to the second switching array 114. The remainder of the electrodes on leads 16, 32, 52 that are not coupled to FETs 118 may be coupled to a second plurality of field effect transistors 120a-c (collectively "FETs 120") and a third plurality of field effect transistors 121a-c (collectively "FETs 121"). In the present embodiment, the FETs 120 are used in a switching application. The FET control unit 124a ties the gates of the appropriate FETs 120 to a potential at or above the turn-on voltage for the FET ("ON") or to the most negative voltage in the system ("OFF"). A benefit of this configuration is that the resulting circuit provides the flexibility to select the particular therapy combination on lead 52 that minimizes phrenic nerve stimulation.

The source pins on the FETs 120 and FETs 121 are coupled to a plurality of ground-path switches 116a1-a3 and 116b (collectively "switch 116"). The gate pins of the FETs 121 are coupled to VDD, while the gate pins of the FETs 120 are coupled to a FET control unit 124a. FET control unit 124a receives a signal from controller/timer circuit 71 to selectively close a switch (not shown) that will either power "ON" or power "OFF" the FETs 120. The signals controlling the operation of the FET control unit 124a may be generated based on the decode look-up table, Table 1, illustrated in FIG. 8.

The FETs 118, 120 and 121 provide protection to the pace and sense circuitry in the IMD 14 from external and internal energies. The protection stems from the nature of FET devices, i.e., when the voltage on the drain connection approaches (and exceeds) the V+voltage on the gate (as with a defibrillation event), the FETs turn "off" and prevent the energy from entering the IMD 14.

To complete the circuit path for the charging of the tip capacitor 104, controller/timer circuit 71 controls the turning "ON" of the appropriate one or more of FETs 120 as well as toggling the corresponding switch 116. The powering of the appropriate FETs 120 and closing the appropriate switch 116, a complete circuit path is created. In effect, the circuit path allows current to pass from a first electrode through the heart 10 as the tip capacitor 104 is being charged and back through a second electrode to ground thereby providing the stimulus.

After the first phase of the therapy delivery, which results in charging of the tip capacitor 104, an appropriate ground switch 112a-c that was open during the first phase is closed to initiate the second phase of the therapy delivery. It should be kept in mind that appropriate switch on first switching array 110 is left open during the second phase. The second phase delivers a therapy having a second polarity (positive, in this embodiment) that is opposite to the first polarity that was delivered during the first phase. The second phase causes the discharge of the tip capacitor 104 with the charge on the tip capacitor 104 flowing through the heart 10 in the same manner as described in conjunction with the first phase. Accordingly, a path to ground for discharge of one of tip capacitors 104 across the connected electrode pair is provided. In this manner, a therapy (including both positive and negative polarities) such as a pacing pulse with a given pulse amplitude is delivered to heart 10 via the electrode pair.

By way of summarizing the therapy delivery aspects of the present disclosure, during the first phase of a pace therapy stimulus, for example, the previously charged hold capacitor 102 is connected in series with the tip capacitor 104 and the appropriate electrode on one of the leads 16, 32, 52. The uncharged tip capacitor 104 is charged from the hold capacitor 102 with the current passing through the electrodes on heart 10 (e.g., tip-ring electrodes) to provide the therapy stimulus. The second phase decouples hold capacitor 102 and couples the negative terminal of tip capacitor 104 to ground allowing the tip capacitor 104 to discharge. Again, this current passes through the heart 10 to provide therapy stimulus having an opposite polarity.

As further illustrated in FIG. 3, the source pins of FETs 118, FETs 121, and FETs 120 are coupled to a protective circuitry 122a-g that provides protection of the various components of output circuit 84a and beyond. The illustrative protective circuitry 122a-g comprises a pair of clamping diodes with a filtering capacitor. Therefore, in addition to providing protection of the various components, unwanted noise may be filtered through the capacitor in the protective circuitry 122a-g thereby improving the sensing capability and sensitivity of the IMD 14.

FIG. 4 depicts an alternative embodiment of an output circuit 84b. The elements of output circuit 84b corresponding to those of output circuit 84a are numbered with identical reference designators. The reader is referred to the preceding description of FIG. 3 for a full discussion pertaining to those components. The implementation of output circuit 84b shows an embodiment where the tip capacitor is connected to one of the lead electrodes by switching the appropriate FET gate "ON." In an alternative embodiment, an increase in the ability to provide field steering on a single lead may be achieved by coupling multiple electrodes on the lead to the therapy output channel defined by the selected hold and tip capacitors. For example, in output circuit 84b, two electrodes on lead 52 can be actively coupled to the second switching array 114 for energy delivery during the first phase.

Turning then to FIG. 4, four electrodes on lead 52 are coupled to the second switching array 114 through field effect transistors 126a-d (collectively "FETs 126"). In the embodiment, the gate pins of the FETs 126 are coupled to FET control unit 124b, while the source pins on the FETs 126 are paired and together are coupled to the second switching array 114 through two traces. By combining the signals from two of the FETs 126, i.e., FET 126a with 126c and FET 126b with 126d, the switch count required at the switching array 114 is reduced as compared to an implementation with direct coupling of each FET with single traces. FET control unit 124b ties the gates of the FETs 126 to a potential at or above the turn-on voltage for the FET ("ON") or to the most negative voltage in the system ("OFF"). The FET control unit 124b provides increased flexibility in the dynamic control of the FETs 126 because any desired combination of the FETs 126 can be turned "ON" or "OFF" at any given time. As such, FET control unit 124b may receive a signal from controller/timer circuit 71 to selectively close a switch (not shown) that will either power "ON" or power "OFF" the FETs 126. The signals controlling the operation of the FET control unit 124b may be generated based on the decode look-up table, Table 2, illustrated in FIG. 9.

The source pin terminals of FETs 126 are also coupled to the ground-path switch 116b to complete the circuit path across the connected electrode pair during the first therapy delivery phase. The second switching array 114 operates in conjunction with the ground-path switch 116b to either couple the FETs 126 to the tip capacitors 104 or to the circuit's ground terminal. As such, by powering the desired one of FETs 126 and closing the appropriate switch 116b, a ground-path is created. Here again, the number of switches required at ground-path switch 116b in this exemplary implementation is reduced in comparison to FIG. 5 because of the pairing of the signals from the source pins on the FETs 126.

FIG. 5 depicts yet another embodiment of an output circuit 84c. Here, again, the elements of output circuit 84c corresponding to those of output circuit 84a in FIG. 3 are numbered with identical reference designators. Output circuit 84c illustrates one implementation for coupling an additional hold capacitor 102d to provide a total of four hold capacitors 102 and an additional tip capacitor 104d for a total of four tip capacitors 104. Of course, the circuit in this and other embodiments can be modified as necessary to include fewer or more hold and tip capacitors and there is no requirement that the number of hold capacitors be identical to the number of tip capacitors. As discussed above, the tip capacitor 104d is placed in parallel with a zener diode 106d to prevent the potential for application of reverse voltages.

The tip capacitors 104 are coupled to the second switching array 114 that may include an additional switch 114d. In the implementation, all four electrodes on lead 52 are coupled to the second switching array 114. Specifically, the second switching array 114 is coupled to a plurality of field effect transistors 128a-f (collectively, "FETs 128") and the four electrodes on lead 52 are each coupled to one of the FETs 128 with the remaining two FETs 128 being coupled to the electrodes on leads 16 and 32. The increased active electrode coupling, of the electrodes on lead 52, achieved by this implementation provides greater flexibility of therapy field steering by selecting different electrode combinations.

Additional switches are also provided on ground-path switch 116b1-b3 to provide a ground path for each of the four electrodes on lead 52. The switches on ground-path switch 116b operate in conjunction with the switches on second switching array 114 such that the each of the source pin terminals can be independently controlled to either be electrically coupled to ground (zero voltage) or to the tip capacitor 104.

As illustrated in FIGS. 4 and 5, the implementations may lead to an increase in the number of switches and/or FETs in the output circuits 84b-c as compared to the output circuit 84a of FIG. 3. However, those implementations (output circuits 84b-c) provide an increase in the dynamic control of the active electrodes in the lead 52. Thus, like the output circuit 84a, output circuits 84b-c may suitably be employed in conjunction with a quadripolar lead with increased selection of active electrode combinations which increases the ability to perform field steering. As such, depending on the desired outcome, various sections of the output circuits 84a-c may be combined in a given implementation utilizing dynamic control and switching functionality to create non-dedicated therapy output channels. Accordingly, numerous additional implementations can be envisioned that deviate from the implementations discussed in the present disclosure which still conform to the general principles discussed herein.

While not shown in FIGS. 3-5 for ease of illustration, it should be appreciated that the first switching array 110, the first ground switch 112a-c, the second switching array 114, the ground-path switch 116 and FET control units 124a-b may be coupled to digital controller/timer circuit 71. Digital controller/timer circuit 71 issues control signals that control which, if any, of the hold capacitors 102 is coupled with one of the tip capacitors 104 through actuation of the appropriate switches on the first switching array 110 and the ground switch 112a-c. In this manner, digital controller/timer circuit 71 controls independent delivery of therapy by the defined therapy output channel. As previously noted, the pair formed by hold capacitor 102 and tip capacitor 104 through controlled selection by digital controller/timer circuit 71 defines a pacing channel for delivery of therapy stimulus. Additionally, digital controller/timer circuit 71 determines the electrodes to which the pacing channel is coupled and hence the electrodes that will deliver the therapy stimulus. In other words, digital controller/timer circuit 71 independently controls the position of each of the switches in the switching arrays as well as whether the FETs are turned "ON" to provide a versatile circuit that is responsive to various combinations of control signals to achieve different combinations of components therein.

Figure 6:
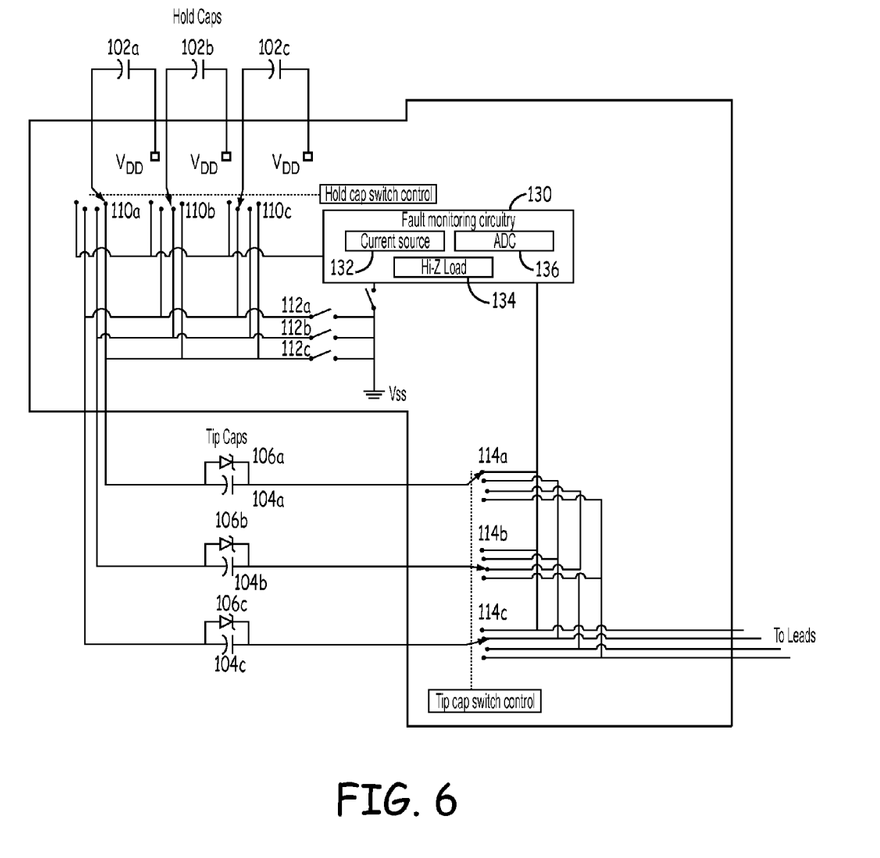
FIG. 6 illustrates an exemplary embodiment of a circuit diagram for a fault detection circuit.

An additional aspect of each of the output circuits 84a-c comprises a fault detection circuit 130. For purposes of clarity, the exemplary configuration of fault detection circuitry 130 and its coupling to the components within output circuits 84 is shown in FIG. 6. Briefly, fault detection circuitry 130 functions to monitor the components of output circuits 84 in order to detect any abnormalities associated with the operation of the components. In response to detecting a component abnormality, fault detection circuitry 130 transmits a signal to the controller/timer circuit 71, with the signal being utilized in one embodiment to reconfigure the coupling of the components in output circuits 84 such that the component(s) that are determined to exhibit an abnormality are switched out of the output circuits 84.

Turning to FIG. 6, a circuit diagram of an embodiment of a fault detection circuit is illustrated. Fault detection circuitry 130 may be utilized to monitor any of the components of output circuit 84. In the exemplary embodiment of the detection circuitry 130, the hold capacitors 102 and tip capacitors 104 are monitored to determine whether any of those capacitors are exhibiting an abnormality. Although abnormalities in the operation of capacitors are unexpected, those skilled in the art are familiar with instances when a capacitor operates in less than ideal conditions. The exemplary detection circuitry 130 is thereby employed to detect when one of the capacitor's operation is deemed abnormal and provides a signal to the microcomputer circuit 64 identifying that capacitor to limit or even exclude it from use in defining a therapy output channel.

Fault detection circuit 130 includes a current source 132, a high impedance load 134 and a comparator or an analog-to-digital converter (ADC) 136. The current source 132 may be coupled in series with the high impedance load 134 which in one embodiment may simply be a resistor. The ADC 136 may be coupled to measure the voltage or current of the hold and tip capacitors in the output circuit 84. The measure of the voltage or current of the capacitor is then sent to the controller/timer circuit 71 to determine whether the capacitor is exhibiting an abnormality. As such, the baseline (normal) characteristics of each of the hold and tip capacitors may be programmed into the microcomputer circuit 64 so that it can be determined whether the measured current or voltage is within the normal range. In conjunction with the fault detection circuit 130, the microcomputer circuit 64 may provide signals to control the first switching array 110 and second switching array 114 to select the desired hold or tip capacitor to be monitored. Microcomputer circuit 64 also determines the exact timing at which the capacitor monitoring will be performed including the intervals for the monitoring while also selecting the hold and tip capacitor combination for therapy delivery. In exemplary embodiments, one or more of the hold and tip capacitors is switched in and out of the circuit as necessary to perform the current or voltage measurements based on control signals provided via the controller/timer circuit 71 from microcomputer circuit 64.

Operationally, the exemplary detection circuitry 130 will typically charge each of the hold capacitors 102 and tip capacitors 104, individually. Detection circuitry 130 then measures the voltage on the charged test capacitor after a predetermined amount of time has elapsed. The measured voltage is then compared to the amount of charge to which the capacitor was initially charged to determine how much charge leaked off. In one implementation, this process would be repeated for each capacitor in a round-robin fashion at regular intervals with the exact timing depending on the implementation. In accordance with aspects of this disclosure where the hold capacitors 102 and tip capacitors 104 are non-dedicated, the fault detection scheme is easily implemented because the capacitors forming a therapy output channel can be switched in and out as desired to perform the measurements.

An alternate implementation may include an alarm (not shown) to generate a notification in response to the signal generated by detection circuitry 130 indicating an abnormality with a component. Such alarms are known in the art and they generally provide audible, tactile or vibratory signals to alert the patient/physician. One example illustrating such alarms can be found in U.S. Pat. No. 6,082,367, "Audible sound communication from an implantable medical device" issued to Greeninger et al., which is incorporated herein by reference in its entirety. Additionally, telemetry functionality may be employed to communicate to an external device (not shown) the determination of a component abnormality in the implantable device.

Figure 7:
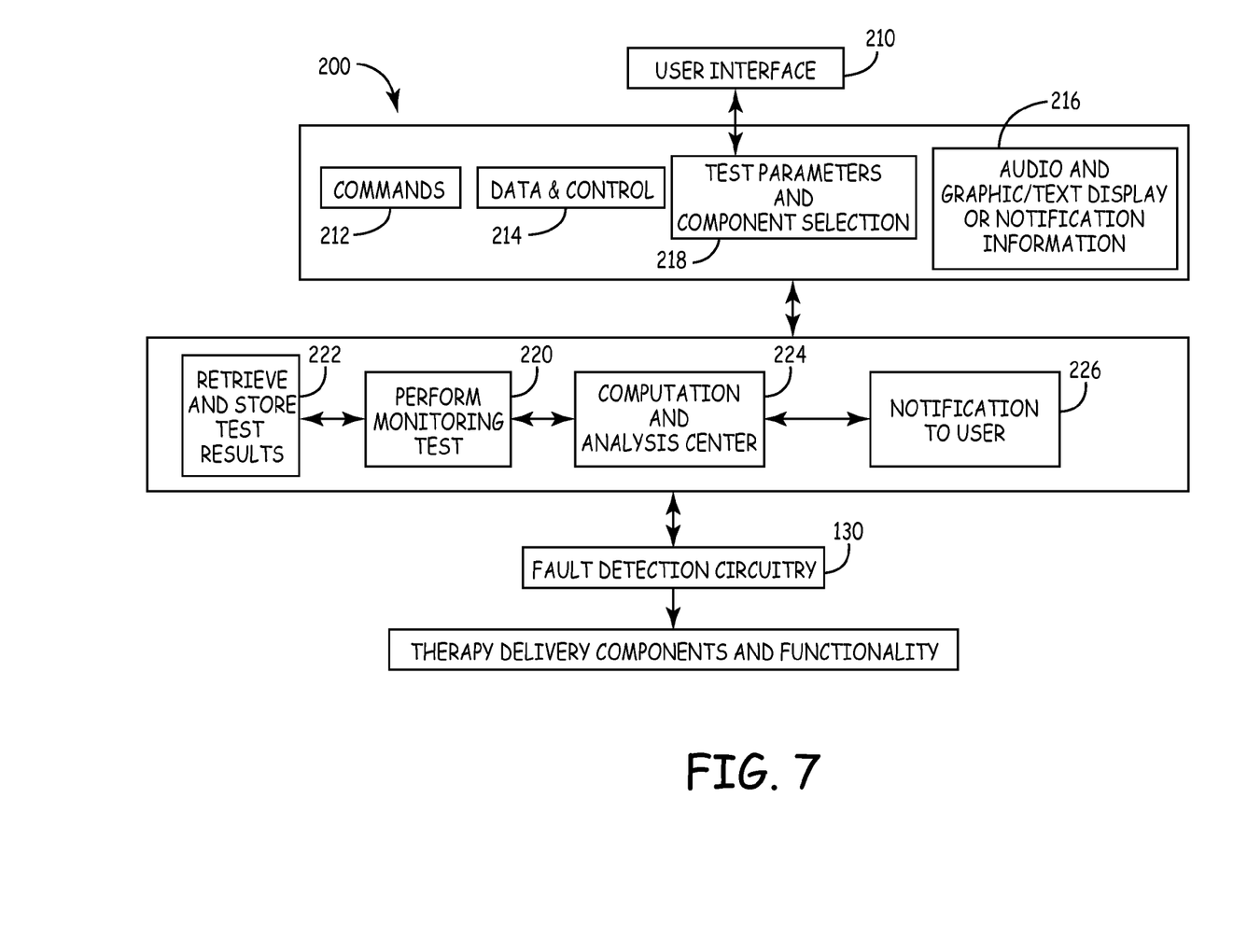
FIG. 7 is a functional block diagram illustrating an embodiment of a system for performing fault-detection with graceful degradation of circuit functionality.

FIG. 7 is a functional block diagram illustrating an embodiment of a system for performing fault-detection with graceful degradation of circuit functionality. The fault-detection system 200 may be implemented as an algorithm in IMD 14 or as a multi-part system that is implemented partially in IMD 14 and partially in an external device that is in communication with IMD 14. The system 200 interacts with the controller/timer circuit 71 and output circuits 84, and in particular, the fault detection circuitry 130.

In the particular embodiment illustrated, a user interface 210 is provided to facilitate user-interaction with the IMD 14 for information entry and presentation. The information entered includes commands to initiate and terminate testing, as well as data and control parameters for the system 200. The data parameters can include information pertaining to each component, the function of the component, and other data associated with a component. Control parameters may include frequency of component monitoring, duration of component monitoring, type of component to be monitored and the test associated with a given component. The user-entered information may additionally be stored within IMD 14 in a form comprising instructions to be implemented by the controller/timer circuit 71. The information provided to the user may include notifications about abnormalities detected by the fault-detection system 200 and the nature of action taken by the system 200 such as circuitry reconfiguration to redefine therapy output channels. Other types of notifications can be made such as the monitored component did not exhibit any abnormality, there is an issue with a component, a recommendation concerning the component, or a function of the IMD 14 has been disabled due to an indication of abnormality and this information can be conveyed graphically to the user at the user interface 210.

At block 218 component monitoring parameters associated with the component to be monitored are selected and are stored until needed to perform the monitoring test. For example, in the case of a capacitor, the parameters may include the voltage associated with each capacitor and the corresponding charge leakage curve. When the system 200 is ready to perform the test, it performs a component monitoring test at block 220 and retrieves data indicating the results of the test. This test is performed in conjunction with the fault detection circuitry 130. Block 220 will implement control parameters which define the monitoring conditions under which the test is performed, retrieve the measurements, and store the collected data in memory.

That collected data information is stored at 222 and can be communicated to computation and analysis center 224, which performs intelligence on the measured component data. The computation and analysis center 224 will control the hold capacitor to tip capacitor configurations, trigger and control the component testing, determine abnormalities associated with the components and provide notifications to user interface 210. The computation and analysis center 224 provides the intelligence to automatically perform decision making, which will lead to immediate reconfigurations without clinician involvement. In various embodiments, the capacitor and component configurations are controlled via the FETs and switches of the switching arrays, ground, ground-paths and FET control unit. These switches and FETs receive control signals from controller/timer circuit 71 via the control lines 85 with the input for these signals originating from computation and analysis center 224. As such, the computation and analysis center 224 dynamically controls the switches and gates of the FETs so that only the desired capacitors are used to define therapy output channels and only the desired FET combinations are "ON." An additional benefit of individual control of the FETs is that flexibility to select different electrode combinations (including tip-ring, ring-tip, and ring-ring) is achieved. Adjustments and decisions will be communicated to the clinician 226 and any subsequent changes to the configuration can be initiated by the user through the user interface 210 as required.

The computation and analysis center 224 can perform mathematical manipulations and calculations based on the measurement and input parameters measured. If the test reveals a potential abnormality, center 224 can initiate a change in the configuration of the components. For example, the configuration changes described in Table 3, below, can be made to achieve graceful degradation of functionality where the abnormality is associated with capacitors or charging pumps (not shown).

TABLE 3

| Abnormality | Degraded operation |
| --- | --- |
| One failed hold and/or tip capacitor | System detects capacitor with abnormality and removes it from use. Remaining capacitors are sufficient to maintain operation with no degradation. A notification of the abnormality and action taken is sent to the user. |
| Two failed hold and/or tip capacitor | System detects the capacitors with abnormalities and removes them from use. The capacitor initially configured for the atrial therapy |

TABLE 3-continued

| Abnormality | Degraded operation |
|---|---|
| | delivery is recharged during the AV interval and reused for the appropriate ventricular therapy delivery. If capture management is on, the output amplitude is increased. A notification of the abnormality and action taken is sent to the user. |
| Three failed hold and/or tip caps | System detects the capacitors with abnormalities and removes them from use. The capacitor initially configured for the atrial therapy delivery is recharged during the AV interval and reused for the appropriate ventricular therapy delivery. If the capture management feature is on, the output amplitude is increased. A notification of the abnormality and action taken is sent to the user. |
| Charging Pump failure | System uses the battery and NVDD (negative supply voltage) to charge the hold capacitors. As such, the hold capacitor 102 is connected to the positive ($V_{DD}$) terminal of battery 72 for charging. A notification of the abnormality and action taken is sent to the user. |

The embodiments of the disclosure provide the ability to search, discover, and capture patterns of component abnormalities that will affect the delivery of therapy. The aspects of these embodiments provide multiple levels of fault tolerance with graceful degradation of functionality. As can be appreciated, the fault detection and graceful degradation system can be implemented for monitoring and resolving component failures not associated with capacitors and the charging pump. The system can be implemented to reconfigure the circuitry for abnormalities associated with other components such as switches. For example, the illustrative embodiments include multiple switches that are implemented to provide redundancy such that any two components can be coupled via any of the available switches and hence failure of one switch would simply require reconfiguring the switch through which the signals are sent.

Figure 8:
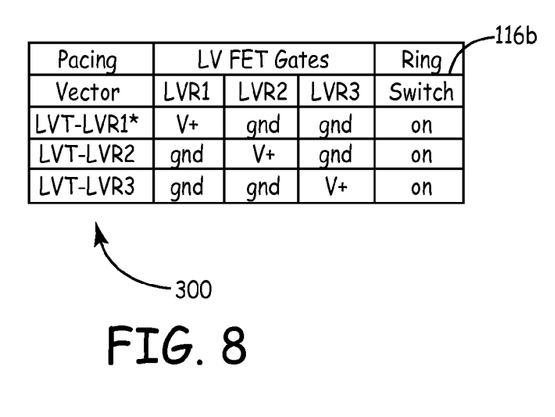
FIG. 8 illustrates one embodiment of a look-up table that may be utilized in conjunction with a transistor control unit in accordance with principles of this disclosure.

FIG. 8 illustrates one embodiment of a look-up table that may be utilized in conjunction with the FET control unit 124a of FIG. 3. The look-up table 300 may be stored in computer readable medium associated with the microcomputer 64 and accessed to determine whether a given switch should be turned ON or OFF to form any of the illustrated pacing vectors. In the look-up table 300, reference to "V+" indicates that the switch is toggled to the positive voltage line while "gnd" indicates that the switch is coupled to the ground signal. Accordingly, to obtain the first vector shown in the first column, LVT-LVR1, the switches associated with the LVR1, LVR2 and LVR3 electrodes are coupled to V+, gnd, and gnd, respectively during the therapy delivery. As was previously explained, the ground path is established by coupling ground-path switch 116b to the ground signal line.

Figure 9:
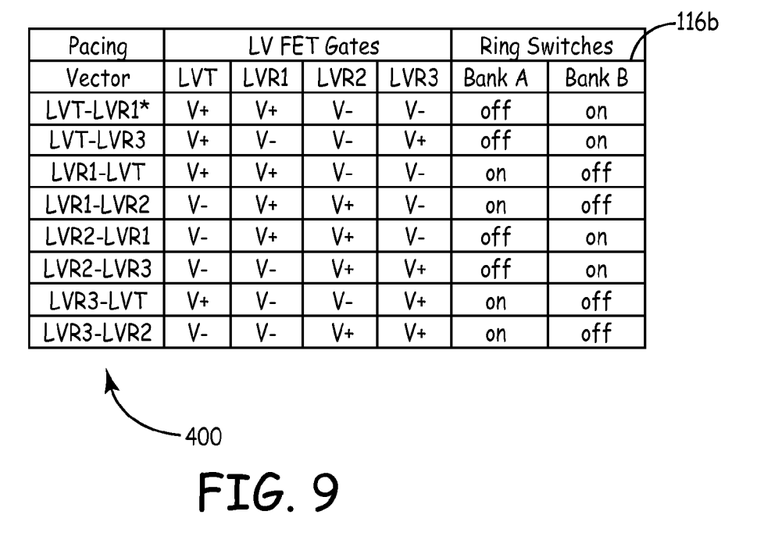
FIG. 9 illustrates one embodiment of a look-up table that may be utilized in conjunction with another transistor control unit in accordance with principles of this disclosure.

FIG. 9 illustrates one embodiment of a look-up table that may be utilized in conjunction with the FET control unit 124b of FIG. 4. The look-up table 400 may be stored in computer readable medium associated with the microcomputer 64 and is accessed to determine whether a given switch should be turned ON or OFF to form any of the pacing vectors illustrated in the look-up table 400. In the look-up table 400, "V+" indicates that the switch is toggled to the positive voltage signal while "V-" indicates that the switch is coupled to the most negative voltage in the circuit. With respect to the ground path switch 116b, bank a and bank b, the "on" indicates that the switch is coupled to the ground line while "off" indicates that the switch is disconnected from the ground line. As previously explained, the look-up table 400 depicts that the embodiment of FIG. 4 provides several more pacing vectors as compared to those in the embodiment of FIG. 3. To obtain the first vector shown in the first column of look-up table 400, LVT-LVR1, the LVT, LVR1, LVR2, and LVR3 switches are connected to the V+, V+, V- and V-terminals, respectively, during the therapy delivery. The ground path is established by toggling the ground path switches 116b, bank A and bank b, to off and on, respectively.

The preceding specific embodiments are illustrative of the practice of the aspects of the disclosure. Various modifications can be made without departing from the scope of the claims. For example, the disclosure can be practiced by a variety of implantable medical devices. Simple modifications can also be employed to deliver multiple contemporaneous and simultaneous stimulation therapy signals through one or more electrodes on one or more leads. The disclosure can be embodied as a computer-readable medium that includes instructions for causing a programmable processor to carry out the methods described above. A "computer-readable medium" includes but is not limited to read-only memory, flash memory and a magnetic or optical storage medium. The instructions can be implemented as one or more software modules, which can be executed by themselves or in combination with other software. These and other embodiments are within the scope of the following claims.

What is claimed is:

1. An implantable medical device having a fault tolerant circuit for controlling delivery of a stimulus therapy signal, comprising:
 a stimulus therapy generator for generating the stimulus therapy signal;
 a therapy output circuit including a plurality of hold capacitors and a plurality of tip capacitors coupled to the stimulus therapy generator and further having:
  a plurality of therapy output channels, wherein any one of the plurality of therapy output channels is selectively coupled to the stimulus therapy generator to deliver stimulus therapy signal to a patient;
  a first switching array having at least one switch selected from a plurality of switches, wherein the at least one switch in the first switching array is controlled to selectively couple:
   a first of the plurality of hold capacitors to either a first or a second of the plurality of tip capacitors during a first period to define a first of said therapy output channels, or
   a second of the plurality of hold capacitors to either the first or the second of the plurality of tip capacitors during a second period to define a second of said therapy output channels; and
 control circuitry coupled to the therapy output circuit for generating a trigger signal to control the selective coupling to define the first or second of the plurality of therapy output channels.

2. The implantable medical device of claim 1, further comprising fault detection circuitry configured to monitor the therapy output circuit to detect an operational abnormality, wherein the control circuit generates the trigger signal based on detection of fault by the fault detection circuitry.

3. The implantable medical device of claim 2, wherein the first switching array selectively couples one of the plurality of hold capacitors to one of the plurality of tip capacitors in response to the trigger signal.

4. The implantable medical device of claim 2, wherein the fault detection circuitry is operable to monitor the integrity of each of the hold capacitors and the tip capacitors.

5. The implantable medical device of claim 2, wherein the fault detection circuitry is operable to monitor the integrity of a component of the therapy output circuit.

6. The implantable medical device of claim 5, wherein the trigger signal is generated in response to failure of one of the components of the therapy output circuit.

7. The implantable medical device of claim 5, further comprising an alarm for generating a notification in response to detection of an abnormality of the monitored component, wherein the alarm is selected from the group consisting of a tactile signal, a vibratory signal, and an auditory signal.

8. The implantable medical device of claim 5, further comprising means for transmitting a notification to an external device in response to detecting an abnormality of the monitored component.

9. The implantable medical device of claim 2, wherein the fault detection circuitry further comprises
means for measuring a voltage across the charged hold or tip capacitor over a predetermined period of time.

10. The implantable medical device of claim 9, further comprising means for charging one of the plurality of hold and tip capacitors.

11. The implantable medical device of claim 1, further comprising:
a second switching array disposed within the therapy output circuit; and
a plurality of leads coupled to the second switching array, the second switching array being operable to control the coupling of one of the plurality of leads to the defined therapy output channel.

12. The implantable medical device of claim 11, further comprising:
a third switching array coupled to the second switching array; and
a plurality of electrodes coupled to the third switching array, the third switching array being operable to control the coupling of one of the plurality of electrodes to the second switching array.

13. The implantable medical device of claim 12, wherein the third switching array comprises:
a plurality of transistors coupled to one of the plurality of electrodes, wherein the control circuitry is coupled to the plurality of transistors, and the control circuitry being operable to activate at least one of the plurality of transistors.

14. The implantable medical device of claim 12, wherein the third switching array is operable to control the coupling of the second switching array to at least two of the plurality of electrodes to define one or more pacing vectors.

15. The implantable medical device of claim 1, further comprising controlling the at least one switch of the first switching array to switch the selection of the one of the first or second tip capacitors to a third tip capacitor responsive to detection of a failure of the first or second tip capacitors, and wherein the third tip capacitor is coupled to the first hold capacitor.

16. An implantable medical device system, comprising
means for generating a stimulus therapy;
a therapy output circuit having a plurality of therapy output channels, wherein any one of the plurality of therapy output channels is selectively coupled to the means for generating the stimulus therapy to deliver stimulus therapy signal to a patient, the therapy output circuit including a plurality of hold capacitors and a plurality of tip capacitors, and wherein each of the plurality of therapy output channels is formed by selectively coupling any one of at least a first and a second of the plurality of hold capacitors to any one of at least a first and a second of the plurality of tip capacitors, the circuit being connected to the stimulus therapy generating means;
means for coupling one of the plurality of therapy output channels to the stimulus therapy generating means;
means for detecting a fault in a component of the therapy output circuit; and
control means for generating a trigger signal to control the coupling means to couple the one of the plurality of therapy output channels to the means for generating the stimulus therapy, wherein the selection of the one of the first or second tip capacitors is switched to a third tip capacitor responsive to detection of a failure of the first or second tip capacitors, and wherein the third tip capacitor is coupled to the first hold capacitor.

17. The implantable medical device system of claim 16, further comprising means for generating an alarm in response to detection of the component failure.

18. The implantable medical device system of claim 16, wherein the plurality of therapy output channels are arranged to perform the same or similar function.

19. The implantable medical device system of claim 16, wherein the coupling means includes a plurality of switching arrays.

20. The implantable medical device system of claim 19, wherein the coupling of the first hold capacitor to the first tip capacitor comprises actuating one or more switches of one or more of the switching arrays.

21. A method comprising:
providing a plurality of hold capacitors and a plurality of tip capacitors;
selecting any one of at least a first and a second hold capacitors from the plurality of hold capacitors;
selecting any one of at least a first and a second tip capacitors from the plurality of tip capacitors;
coupling the selected hold capacitor to the selected tip capacitor;
performing a test of the integrity of the plurality of hold capacitors and the plurality of tip capacitors to detect a failure, and
switching the selection of the first tip capacitor to select a second tip capacitor in response to detection of a failure of the first tip capacitor and coupling the first hold capacitor to the second tip capacitor.

22. The method of claim 21, further comprising switching the selection of the first hold capacitor to select a second hold capacitor in response to detection of a failure of the first hold capacitor and coupling the second hold capacitor to the first tip capacitor.

23. The method of claim 21, further comprising providing a notification in response to detection of the failure.

24. The method of claim 21, further comprising coupling an energy delivery source to the first hold capacitor for delivery of a therapy to a patient through the first tip capacitor.

25. The method of claim 21, further comprising decoupling the first hold capacitor from the first tip capacitor in response to detection of the failure and directly coupling the first tip capacitor to the energy delivery source.

26. The method of claim 21, wherein the first tip capacitor is coupled to an electrode for delivery of a therapy to a patient.

27. An implantable medical device having a fault tolerant circuit for controlling delivery of a stimulus therapy signal, comprising:
- a stimulus therapy generator for generating the stimulus therapy signal;
- a therapy output circuit including a plurality of hold capacitors and a plurality of tip capacitors coupled to the stimulus therapy generator and further having:
  - a plurality of therapy output channels for coupling of said stimulus therapy signal to a patient, any one of the plurality of hold capacitors and any one of the plurality of tip capacitors being selectable to define any one of the plurality of therapy output channels;
  - a first switching array having at least one switch selected from a plurality of switches, wherein the at least one switch in the first switching array is controlled to selectively couple:
    - a first of the plurality of hold capacitors to either a first or a second of the plurality of tip capacitors during a first period to define a first of said therapy output channels, or
    - a second of the plurality of hold capacitors to either the first or the second of the plurality of tip capacitors during a second period to define a second of said therapy output channels; and
- control circuitry coupled to the therapy output circuit for generating a trigger signal to control the selective coupling to define the first or second of the plurality of therapy output channels.

28. The implantable medical device of claim 27, wherein the first switching array selectively couples one of the plurality of hold capacitors to one of the plurality of tip capacitors in response to the trigger signal generated by the control circuitry.

29. The implantable medical device of claim 27, further comprising fault detection circuitry operable to monitor the integrity of each of the hold capacitors and the tip capacitors.

30. The implantable medical device of claim 27, further comprising fault detection circuitry is operable to monitor the integrity of a component of the therapy output circuit.

31. An implantable medical device having a fault tolerant circuit for controlling delivery of a stimulus therapy signal, comprising:
- a stimulus therapy generator for generating the stimulus therapy signal;
- a therapy output circuit including a plurality of hold capacitors and a plurality of tip capacitors coupled to the stimulus therapy generator and further having:
  - a plurality of therapy output channels for coupling of said stimulus therapy signal to a patient;
  - a first switching array coupled to the plurality of therapy output channels, wherein one of the switches in the first switching array is controlled to couple any one of at least a first and a second of the plurality of hold capacitors to any one of at least a first and a second of the plurality of tip capacitors to define one of said therapy output channels, wherein the first switching array directly connects the selected one of the plurality of hold capacitors to the selected one of the plurality of tip capacitors; and
- fault detection circuitry coupled to the therapy output circuit for generating a trigger signal to control the coupling between the plurality of therapy output channels and the stimulus therapy generator, wherein the at least one switch of the first switching array is controlled to switch the selection of the one of the first or second tip capacitors to a third tip capacitor responsive to detection of a failure of the first or second tip capacitors, and wherein the third tip capacitor is coupled to the first hold capacitor.

32. An implantable medical device having a circuit for controlling delivery of a stimulus therapy signal, comprising:
- a stimulus therapy generator for generating the stimulus therapy signal;
- a therapy output circuit including a plurality of hold capacitors and a plurality of tip capacitors coupled to the stimulus therapy generator and further having:
  - a plurality of therapy output channels, wherein any one of the plurality of therapy output channels is selectively coupled to the stimulus therapy generator to deliver stimulus therapy signal to a patient;
  - a first switching array having at least one switch, wherein the at least one switch in the first switching array is controlled:
- to selectively couple a first of the plurality of hold capacitors to either a first or a second of the plurality of tip capacitors during a first period to define a first of said therapy output channels, or
- to selectively couple a second of the plurality of hold capacitors to either the first or the second of the plurality of tip capacitors during a second period to define a second of said therapy output channels; and
- control circuitry coupled to the therapy output circuit for generating a trigger signal to control the selective coupling to define the first or second therapy output channels.

* * * * *